(12) United States Patent
Jackson

(10) Patent No.: US 6,267,844 B1
(45) Date of Patent: Jul. 31, 2001

(54) PROCESS FOR PRODUCTION OF PAPER USING THIOETHER COMPOUNDS

(75) Inventor: Andrew Clive Jackson, Harrogate (GB)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 09/297,446

(22) PCT Filed: Sep. 2, 1998

(86) PCT No.: PCT/IB98/01366

§ 371 Date: Apr. 30, 1999

§ 102(e) Date: Apr. 30, 1999

(87) PCT Pub. No.: WO95/35331

PCT Pub. Date: Dec. 28, 1995

(30) Foreign Application Priority Data

Sep. 2, 1997 (GB) .................................................. 9718530

(51) Int. Cl.$^7$ ........................... D21H 19/42; D21H 19/48
(52) U.S. Cl. ..................... 162/164.5; 162/168.4; 162/177
(58) Field of Search .................. 162/76–77, 78, 162/82, 164.5, 168.4, 177; 427/384; 525/408; 528/360; 536/59; 560/147

(56) References Cited

U.S. PATENT DOCUMENTS 2,559,521 * 7/1951 Smith et al. ........................ 260/484
2,575,196 * 11/1951 Smith et al. ........................ 260/485
6,030,495 * 2/2000 Wan et al. ............................ 162/82

FOREIGN PATENT DOCUMENTS

WO 95/35331 * 12/1995 (WO) .
WO95/35331 * 12/1995 (WO) .

OTHER PUBLICATIONS

Bonnans–Plaisance, C., "Functional . . . Macromonomers", 2445 Polymer Bulletin, pp. 141–147, Feb. 1995.*
Cole, B.J.W., "Bleaching . . . Compounds", TAPPI Journal, pp. 117–122, Nov. 1987.*
Cole, B.J.W "Bleaching and . . . Compounds", TAPPI Journal, pp. 117–122, Nov. 1987.*
Plaisance, C.B. "Functional Polythiiranes 4", ppl. 141–147, Feb. 1995.*

* cited by examiner

*Primary Examiner*—Dean T. Nguyen
(74) *Attorney, Agent, or Firm*—Krishna Banerjee

(57) ABSTRACT

A paper production process, characterized by the process step of providing to the paper at some point in the production process a compound of formula (I)

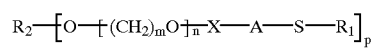

which reduces the tendency of the obtained paper products, particularly those made from high-yield pulps, to yellow on exposure to light.

7 Claims, No Drawings

PROCESS FOR PRODUCTION OF PAPER USING THIOETHER COMPOUNDS

BACKGROUND OF THE INVENTION

This invention relates to the reduction of brightness reversion in paper products, particularly those made from high-yield pulps and to compositions for achieving same.

A "high-yield" pulp is a pulp in which the papermaking fibres are separated by means which are mainly mechanical action (optionally with some chemical treatment). As the name indicates, there is relatively little waste with such a pulp, in contrast to the so-called "chemical" pulps where the fibre separation is achieved by purely chemical means. Paper made from high-yield pulp (for example, groundwood pulp, refiner pulp, thermomechanical pulp (TMP), and chemithermomechanical pulp (CTMP)) is considerably cheaper than that made from chemical pulp, even when the high-yield pulp is bleached. The problem which has restricted the use of high-yield pulps to non-archival uses such as newsprint and corrugated paper is the tendency of such paper to undergo brightness reversion (yellowig) with time, this being believed to be caused by the instability to ultraviolet light of the lignin component of high-yield pulps.

SUMMARY OF THE INVENTION

The present invention provides a process for the production of paper, comprising the steps of: (a) providing a paper pulp, and (b) forming a paper sheet therefrom, the process further including the process step of providing to the paper at some point in the said production process a thioether compound of formula I

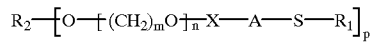
(I)

in which m is an integer of from 2–4;

n is an integer of at least 2;

p is an integer of from 1–4;

X is a bridging member and A is alkylene or arylene, optionally substituted;

$R_1$ is (a) alkyl ($C_1$–$C_6$), optionally substituted but not containing fluorine or silicon, (b) phenyl or benzyl, both optionally substituted or (c) a heteroaromatic residue, and if p is equal to 1 and $R_2$ is hydrogen or alkyl ($C_1$–$C_6$), then $R_1$ can also be another residue $R_3O[(CH_2)_mO]_nX$—A—S—Z— where $R_3$ is hydrogen or alkyl ($C_1$–$C_6$), and Z is selected from $(CH_2)_2$, $(CH_2)_3$, $(CH_2)_4$, $CH_2CH(CH_2OH)$, $CH_2CH(OH)CH(OH)CH_2$, $CH_2CH_2OCH_2CH_2$, 1,2-phenylene, 1,3-phenylene, 1,4-phenylene, 2,5-(1,3,4-thiadiazolyl), 1,3-xylylene, 1,3,5-triazinyl (optionally substituted), and $R_2$ is hydrogen or alkyl ($C_1$–$C_6$), optionally substituted, or another residue $R_1$—S—A—X—.

DESCRIPTION OF THE PREFERRED EMBODIMENTS

It has now been found that the use of certain compounds allows the light-induced yellowing of paper to be considerably reduced, often to levels where papers not previously thought suitable for archival material may be used for such applications. The invention therefore provides a paper production process, comprising the process steps of (a) providing a paper pulp, and (b) forming a paper sheet therefrom, the process further including the process step of providing to the paper at some point in the said production process a thioether compound of formula I

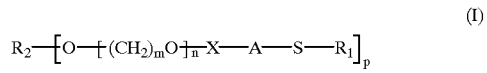
(I)

in which m is an integer of from 2–4;

n is an integer of at least 2;

p is an integer of from 1–4;

X is a bridging member and A is alkylene or arylene, optionally substituted;

$R_1$ is (a) alkyl ($C_1$–$C_6$), optionally substituted but not containing fluorine or silicon, (b) phenyl or benzyl both optionally substituted or (c) a hetaromatic residue, and if p is equal to 1 and $R_2$ is hydrogen or alkyl ($C_1$–$C_6$) then $R_1$ can also be another residue $R_3O[(CH_2)_mO]_nX$—A—S—Z— where $R_3$ is hydrogen or alkyl ($C_1$–$C_6$), and Z is selected from $(CH_2)_2$, $(CH_2)_3$, $(CH_2)_4$, $CH_2CH(CH_2OH)$, $CH_2CH(OH)CH(OH)CH_2$, $CH_2CH_2OCH_2CH_2$, 1,2-phenylene, 1,3-phenylene, 1,4-phenylene, 2,5-(1,3,4-thiadiazolyl), 1,3-xylylene, 1,3,5-triazinyl (optionally substituted), and $R_2$ is hydrogen or alkyl ($C_1$–$C_6$), optionally substituted, or another residue $R_1$—S—A—X—.

Examples of X are —C(=O)—, —$CH_2$C(=O)O—, —C(=O)NH—, —S(=O)$_2$— or a direct bond.

Examples of suitable groups $R_1$ include methyl, ethyl, $CH_3OC(=O)CH_2$—, $CH_3CH_2OC(=O)CH_2$—, $HOCH_2CH_2$—, $CH_3CH(OH)CH_2$— and $HOCH_2CH(OH)CH_2$—.

Examples of suitable groups $R_2$ include H—, methyl, ethyl and $HOCH_2CH_2SCH_2CH_2C(=O)$.

The heteroaromatic residue is selected from 2-thienyl, furfuryl, 2-pyridinyl (optionally substituted), 4-pyridinyl (optionally substituted), 2-(5-methyl-1,3,4-thiadiazolyl), 2-pyrimidyl, 2-(4-hydroxypyrimidyl), 2-(4-hydroxy-6-methylpyrimidyl), 2-(4-hydroxy-6-propylpyrimidyl), 2-(4,6-dihydroxypyrimidyl), 2-benzoxazolyl and 2-benzothiazolyl (optionally substituted).

Preferably and independently of each other m is 2;

n is at least 4, more preferably 4–50;

p is 1;

X is —C(=O)— or —$CH_2$C(=O)O—;

A is methylene or ethylene;

$R_1$ is methyl, ethyl, $HOCH_2CH_2$—, phenyl, benzyl or 1,3,5-triazinyl;

$R_2$ is hydrogen, methyl or $HOCH_2CH_2SCH_2CH_2C(=O)$—.

Compounds of formula I can be produced for example by addition of a compound of the formula II

HS—$R_1$ (II)

to mono- or diacrylate esters of polyalkylene glycols of the formula III

(III)

or by reaction of polyalkylene glycols with compounds of the formula IV

HOC(=O)—A—S—R₁                 (IV)

and optionally further reaction with bridging reactants.

The invention further provides a method for reducing the tendency of a paper to yellow on exposure to light, comprising the incorporation thereinto, at some stage in the manufacture thereof, of a compound according to formula I.

The invention further provides a paper additive which comprises a compound of formula I.

The invention further provides paper produced by a process incorporating a compound of formula I.

In this description of the invention, unless otherwise stated, the description of a component in the singular also includes the possibility that more than one such component may be used.

The paper may also contain other additives known in the art to control brightness reversion. Examples of such additives include ultraviolet absorbers, for example, 2,4-dihydroxybenzophenone, benzotriazole UV absorbers such as "FADEX" (trade mark) F liquid and "TINUVIN" (trade mark) 1130, ascorbic acid, sodium ascorbate, ethylene glycol bisthioglycolate, S-methyl-1-thioglycerol, sodium hypophosphite, poly(ethylene glycol), and poly (tetrahydrofuran). Such additives may be added either together with, or separately from, the thioether compound as hereinabove described. More preferably, the thioether is added together with an ultraviolet absorber.

The paper may further contain other additives commonly employed in the papermaking industry. Examples of such additives include sizing agents (for example, rosin, starch, alkyl ketene dimer, alkenyl succinic anhydride), wet strength resins (for example, polyaminoamide-epichlorohydrin resins), retention- and drainage aids (for example, polyaluminum chloride, polydiallyldimethylammonium chloride), and optical brightening agents. Such additives may be added either together with, or separately from, the thioether.

The invention is performed by adding the thioether to the pulp or paper sheet at some point in the paper production process, and preferably at the size-press. There are a number of possibilities, namely, (a) addition to the pulp, prior to sheet formation;
(b) application to a sheet formed on the wire of a paper machine, for example by spraying or coating;
(c) addition at a size-press;
(d) application to the sized sheet at a stage later than the size-press.

The preferred possibility is (c). In all cases, the total quantity of compound lies between 0.02% and 20% (preferably between 0.1% and 10%) by weight on dry fibre.

The invention may be used with paper made from any kind of pulp, but gives especially good results with papers which are formed from high-yield pulps, whereby, with the use of the invention, the tendency to yellow is reduced to a surprising and considerable degree. This permits the use in paper of much higher quantities of high-yield pulp than was previously the case, with consequent potential for considerable cost savings. Depending on the choice of thioether, other advantages can include all of low cost, thermal stability, water-solubility, low toxicity, low odour and a bleaching effect.

EXAMPLES

Preparative Example 1

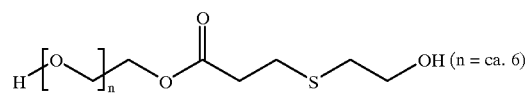

Poly(ethylene glycol) acrylate of average $M_n$ ca. 336 (33.6 g) is cooled to below 10° C. using an ice/water cooling bath. 2-Mercaptoethanol (7.0 g) is added dropwise at such a rate that the temperature does not exceed 25° C. The cooling bath is removed, and the reaction mixture is stirred at ambient temperature for 3 hours, and then at 50° C. for a further 1 hour. 30% Hydrogen peroxide (0.2 g) is added, and heating is continued for a further 1 hour. The compound so-formed is a clear, colourless, odourless liquid.

According to the method described in preparative example 1, further compounds can be synthesized from reactants as indicated in Table 1

TABLE 1

| Ex. | Acrylate with average Mn | Mercaptan | Endproduct |
|---|---|---|---|
| 2 | 469 | 2-Mercaptoethanol | (n = ca. 9) |
| 3 | 254 | 2-Mercaptoethanol | (n = ca. 4) |
| 4 | 336 | Benzylmercaptan | (n = ca. 6) |

TABLE 1-continued

| Ex. | Acrylate with average Mn | Mercaptan | Endproduct |
|---|---|---|---|
| 5 | 336 | 1,2-Ethanediol | 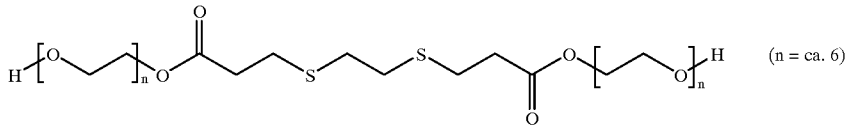 (n = ca. 6) |
| 6 | 708 (diacrylate) | 2-Mercaptoethanol | 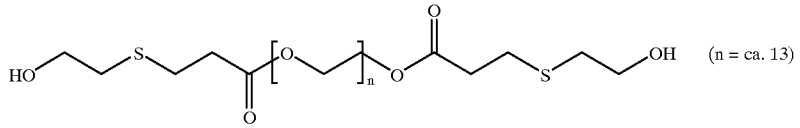 (n = ca. 13) |

Preparative Example 7

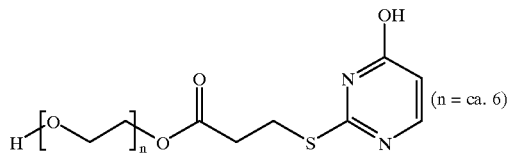 (n = ca. 6)

Poly(ethylene glycol) acrylate of average $M_n$ ca. 336 (33.6 g) is cooled to below 10° C. using an ice/water cooling bath 2-Thiouracil (10.3 g) is added in portions, followed by 30% sodium hydroxide (10.7 g) at a rate such that the temperature does not exceed 25° C. The cooling bath is removed, and the reaction mixture is stirred at ambient temperature overnight. A solution of 30 ml 3M hydrochloric acid is added, and the product is extracted into dichloromethane, dried over sodium sulphate and evaporated to give the above compound as a clear, colourless, odourless liquid.

Preparative Example 8

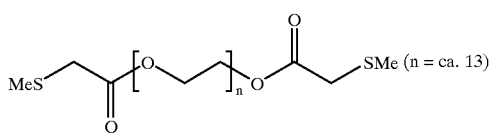 (n = ca. 13)

Ethyl(methylthio)acetate (26.8 g) is added with stirring at 60° C. to poly(ethylene glycol) of average $M_n$ ca. 600 (75.0 g). Dibutyl tin oxide (0.4 g) is added. The mixture is slowly heated to 110–115° C., removing the ethanol formed in the reaction by distillation. After 1 hour at 110–115° C., the reaction vessel is evacuated to 50 mbar. Heating is continued until reaction is complete (10 hours). The vacuum is removed, to leave the above compound as a clear, faintly-coloured, viscous liquid.

Preparative Example 9

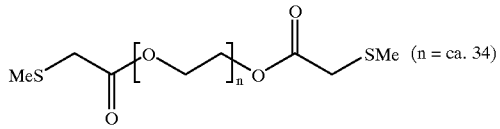 (n = ca. 34)

(Methylthio)acetic acid (50.4 g) is added with sting at 60° C. to poly(ethylene glycol) of average $M_n$ ca. 1500 (375 g). p-Toluenesulphonic acid (2.5 g) is added. The reaction vessel is evacuated to 50 mbar to remove the water formed in the reaction, and the temperature is raised to 95–98° C. After 2 hours at 95–98° C., the temperature is further raised to 130° C. until reaction is complete. The vacuum is removed, to leave the above compound as a clear, faintly-coloured, viscous liquid which solidifies on cooling.

Preparative Example 10

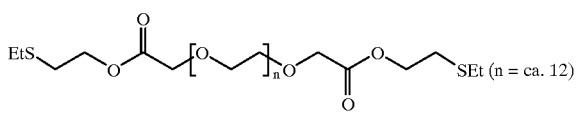 (n = ca. 12)

Ethyl 2-hydroxyethyl sulphide (16.1 g) is added to a stirred solution of poly(ethylene glycol) bis(carboxymethyl) ether of average $M_n$ ca. 660 (53.0 g) in toluene (160 ml). p-Toluenesulphonic acid (0.4 g) is added, and the temperature is raised to reflux. The water formed in the reaction is removed using a Dean and Stark apparat. When reaction is complete, the solvent is removed under reduced pressure to leave the above compound as a clear, faintly-coloured, viscous oil.

Preparative Example 11

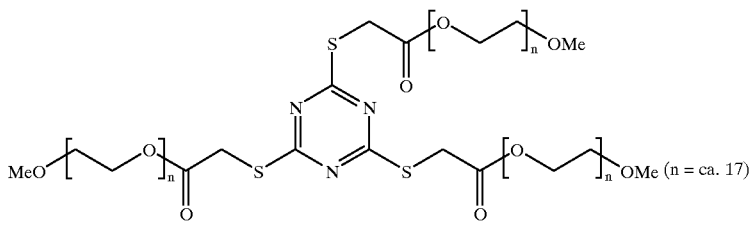

Cyanuric chloride (3.7 g) is added to a stirred mixture of α-mercaptoacetyl-ω-methoxy-poly(ethylene glycol) of average $M_n$ ca. 840 (50.4 g), sodium bicarbonate (5.0 g) and ethanol (40 ml). The mixture is stirred at ambient temperature overnight, filtered and evaporated to leave the above compound as a clear, faintly-coloured, viscous liquid.

Preparative Example 12

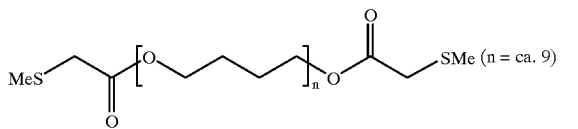

(Methylthio)acetic acid (9.6 g) is added to a stirred solution of TERATHANE® 650 polyether glycol (32.5 g) in toluene (150 ml). 95–98% Sulphuric acid (1 drop) is added, and the temperature is raised to reflux. The water formed in the reaction is removed using a Dean and Stark apparatus. When reaction is complete, the solution is dried over potassium carbonate, and the solvent removed under reduced pressure to leave the above compound as a waxy, white solid.

The invention is illustrated with reference to the following application examples, in which all parts are by weight. The results clearly demonstrate the stabilisation of chemothermomechanical pulp (CTMP) against photo-yellowing provided both by the thioether alone, and by the combination of the thioether with an ultraviolet absorber (Fadex F liquid).

The following coating formulations are prepared as in Table 2.

TABLE 2

| Formulation | Fadex F liquid | Water |
|---|---|---|
| Compound of Example 1 | | |
| 1 | — | 100 parts |
| 2 | 15 parts | — | 85 parts |
| 3 | 15 parts | 4 parts | 81 parts |
| Compound of Example 4 | | |
| 4 | — | 100 parts |
| 5 | 5 parts | — | 95 parts |
| 6 | 15 parts | — | 85 parts |
| Compound of Example 7 | | |
| 7 | — | 100 parts |
| 8 | 4 parts | — | 96 parts |
| 9 | 20 parts | — | 80 parts |
| Compound of Example 5 | | |
| 10 | — | 100 parts |
| 11 | 5 parts | — | 95 parts |
| 12 | 15 parts | — | 85 parts |
| Compound of Example 6 | | |
| 13 | — | 100 parts |
| 14 | 15 parts | — | 85 parts |
| 15 | 15 parts | 4 parts | 81 parts |
| Compound of Example 8 | | |
| 16 | — | 100 parts |
| 17 | 15 parts | — | 85 parts |
| Compound V | Compound of Example 8 | |
| 18 | — | — | 100 parts |
| 19 | 15 parts | — | 85 parts |
| 20 | — | 15 parts | 85 parts |
| Compound of Example 9 | | |
| 21 | — | — | 100 parts |
| 22 | 5 parts | — | 95 parts |
| 23 | 10 parts | — | 90 parts |
| 24 | 10 parts | 2 parts | 88 parts |
| Compound of Example 10 | | |
| 25 | — | — | 100 parts |
| 26 | 5 parts | — | 95 parts |
| 27 | 10 parts | — | 90 parts |
| 28 | 15 parts | — | 85 parts |
| Compound of Example 11 | | |
| 29 | — | — | 100 parts |
| 30 | 6 parts | — | 94 parts |
| 31 | 20 parts | — | 80 parts |
| Compound of Example 1 | | |
| 32 | — | — | 100 parts |
| 33 | 10 parts | — | 90 parts |
| 34 | 15 parts | — | 85 parts |

Application Example 1

Each formulation is applied at the size-press to a handsheet made from bleached chemithermomechanical pulp (CTMP). The treated handsheets are then air-dried for a minimum of 24 hours in a constant temperature and humidity environment and protected from light. Accelerated ageing experiments are conducted by irradiating handsheet samples in a modified fan-cooled "RAYONET" RPR-100 photochemical reactor using 16 RPR-3500 Å lamps (Southern New England Ultraviolet Company). The yellowing process is monitored by taking CIE whiteness measurements at regular intervals using an Elrepho spectrophotometer. The results are given in Table 3; the percentage take-up on dry fibre from each formulation is shown in parentheses.

TABLE 3

|  | Loss in CIE whiteness after | | | | |
|---|---|---|---|---|---|
|  | 5 | 10 | 20 | 30 | minutes |
| Formulation 1 | 25.8 | 37.0 | 48.3 | 53.5 |  |
| Formulation 2 (6.7%) | 22.6 | 34.2 | 43.2 | 49.9 |  |
| Formulation 3 (7.1%) | 17.4 | 25.3 | 34.0 | 38.2 |  |
| Formulation 4 | 25.7 | 36.1 | 47.1 | 56.6 |  |
| Formulation 5 (0.8%) | 24.9 | 32.9 | 42.6 | 51.8 |  |
| Formulation 6 (4.9%) | 19.6 | 27.6 | 37.8 | 42.8 |  |
| Formulation 7 | 26.7 | 37.3 | 49.0 | 53.8 |  |
| Formulation 8 (1.0%) | 24.2 | 34.0 | 42.4 | 48.8 |  |
| Formulation 9 (5.1%) | 16.0 | 24.7 | 34.3 | 38.6 |  |
| Formulation 10 | 25.3 | 36.2 | 48.8 | 56.3 |  |
| Formulation 11 (1.7%) | 24.7 | 34.5 | 45.8 | 53.1 |  |
| Formulation 12 (5.6%) | 21.9 | 32.3 | 40.2 | 46.3 |  |
| Formulation 13 | 29.6 | 37.7 | 50.5 | 57.7 |  |
| Formulation 14 (7.0%) | 26.3 | 33.7 | 44.3 | 50.8 |  |
| Formulation 15 (6.7%) | 17.6 | 26.7 | 32.8 | 39.9 |  |
| Formulation 21 | 26.5 | 37.8 | 47.9 | 57.2 |  |
| Formulation 22 (2.0%) | 25.5 | 36.0 | 45.1 | 55.6 |  |
| Formulation 23 (3.5%) | 21.8 | 31.6 | 40.9 | 46.2 |  |
| Formulation 24 (3.5%) | 17.0 | 26.5 | 35.0 | 41.4 |  |
| Formulation 25 | 28.9 | 37.7 | 48.5 | 53.5 |  |
| Formulation 26 (0.8%) | 25.6 | 33.5 | 45.1 | 50.5 |  |
| Formulation 27 (2.5%) | 23.9 | 31.6 | 42.5 | 48.4 |  |
| Formulation 28 (4.0%) | 22.4 | 29.7 | 38.9 | 45.7 |  |
| Formulation 29 | 24.4 | 37.2 | 48.4 | 55.8 |  |
| Formulation 30 (1.6%) | 24.1 | 33.4 | 44.5 | 51.6 |  |
| Formulation 31 (7.6%) | 21.8 | 29.5 | 40.5 | 44.5 |  |

Application Example 2

Five coating formulations (16, 17 and 32 to 34) are prepared as in Table 2. Each formulation is applied at the size-press to a handsheet made from bleached chemithermomechanical pulp (CTMP). The treated handsheets are then air-dried for a minimum of 24 hours in a constant temperature and humidity environment and protected from light. The handsheet samples are then subjected to normal office light. The yellowing process is monitored by taking CIE whiteness measurements at regular intervals using an Elrepho spectrophotometer. The results are summarised in Table 4; the percentage take-up on dry fibre is shown in parentheses.

TABLE 4

|  | Loss in CIE whiteness after | | | | | |
|---|---|---|---|---|---|---|
|  | 7 | 16 | 28 | 56 | 84 | days |
| Formulation 16 | 9.8 | 17.7 | 25.7 | 39.0 | 55.2 |  |
| Formulation 17 (6.1%) | 4.0 | 5.0 | 8.1 | 13.2 | 24.4 |  |
|  | 28 | 56 | 84 | 112 |  | days |
| Formulation 32 | 15.9 | 20.8 | 24.8 | 30.5 |  |  |
| Formulation 33 (1.6%) | 12.1 | 14.4 | 19.2 | 21.9 |  |  |
| Formulation 34 (6.8%) | 9.3 | 10.3 | 12.1 | 13.5 |  |  |

Comparative Example

There coating formulations (18, 19 and 20) are prepared as in Table 2. Compound V is PGTL$_2$800 as described in WO 95/35331.

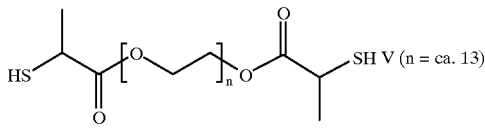

Each formulation is applied at the size-press to a handsheet made from bleached chemithermomechanical pulp (CTMP). The remainder of the experiment is conducted exactly as described in Application Example 1. The results are summarised in Table 5; the percentage take-up on dry fibre from each formulation is shown in parentheses.

TABLE 5

|  | Loss in CIE whiteness after | | | | |
|---|---|---|---|---|---|
|  | 5 | 10 | 30 | 60 | minutes |
| Formulation 18 | 26.8 | 36.1 | 53.9 | 66.7 |  |
| Formulation 19 (6.9%) | 19.4 | 26.3 | 42.2 | 55.9 |  |
| Formulation 20 (6.6%) | 16.1 | 22.4 | 38.0 | 48.9 |  |

Application Example 3

Four coating formulations are prepared as in Table 2. Each formulation is applied at the size-press to a handsheet made from bleached thermomechanical pulp (TMP). The remainder of the experiment is conducted exactly as described in Application Example 1. The results are summarised in Table 6; the percentage take-up on dry fibre from each formulation is shown in parentheses.

TABLE 6

|  | Loss in CIE whiteness after | | | | |
|---|---|---|---|---|---|
|  | 5 | 10 | 20 | 30 | minutes |
| Formulation 25 | 19.0 | 25.1 | 34.6 | 39.6 |  |
| Formulation 26 (3.5%) | 15.2 | 22.1 | 29.0 | 35.1 |  |
| Formulation 27 (6.9%) | 14.6 | 20.1 | 25.8 | 30.4 |  |
| Formulation 28 (10.2%) | 13.7 | 18.0 | 22.5 | 27.7 |  |

Application Example 4

Compound of Example 12 (10% and 20% by weight dry fibre) is stirred for 15 minutes with a 2% aqueous suspension of bleached chemithermomechanical pulp (CTMP). The suspension is then diluted to a concentration of 1%, and formed into handsheets. A blank handsheet is also prepared, from CTMP completely free of test compound. The handsheets are air-dried for a minimum of 24 hours in a constant temperature and humidity environment and protected from light. The remainder of the experiment is conducted exactly as described in Application Example 1. The results are summarised in Table 7.

TABLE 7

| | Loss in CIE whiteness after | | | | |
|---|---|---|---|---|---|
| | 5 | 10 | 20 | 30 | minutes |
| Blank | 27.4 | 36.6 | 47.7 | 57.2 | |
| 10% bwf Compound | 21.2 | 31.7 | 40.7 | 48.4 | |
| 20% bwf Compound | 17.3 | 25.2 | 35.4 | 41.7 | |

What is claimed is:

1. A process for reducing brightness reversion in a paper production process, comprising the process steps of (a) providing a paper pulp, and (b) forming a paper sheet therefrom, the process further including the process step of contacting the paper sheet at some point in the said production process with a compound of formula I:

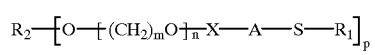

(I)

in which
  m is an integer of from 2–4;
  n is an integer of at least 2;
  p is an integer of from 1–4;
  X is —C(=O)—, —CH$_2$C(=O)O—, —C(=O)NH—, —S(=O)$_2$— or a direct bond, and A is alkylene or arylene;
  R$_1$ is (a) alkyl (C$_1$–C$_6$), (b) phenyl or benzyl, or (c) a heteroaromatic residue, and if p is equal to 1 and R$_2$ is hydrogen or alkyl (C$_1$–C$_6$), then R$_1$ can also be another residue R$_3$O[(CH$_2$)$_m$O]$_n$X—A—S—Z— where R$_3$ is hydrogen or alkyl (C$_1$–C$_6$), and Z is selected from (CH$_2$)$_2$, (CH$_2$)$_3$, (CH$_2$)$_4$, CH$_2$CH(CH$_2$OH), CH$_2$CH(OH)CH(OH)CH$_2$, CH$_2$CH$_2$OCH$_2$CH$_2$, 1,2-phenylene, 1,3-phenylene, 1,4-phenylene, 2,5-(1,3,4-thiadiazolyl), 1,3-xylylene, 1,3,5-triazinyl (optionally substituted), and
  R$_2$ is hydrogen or alkyl (C$_1$–C$_6$), or another residue R$_1$—S—A—X—; wherein the paper sheet, after contact with the compound of formula I, has a reduced tendency to undergo brightness reversion.

2. A process according to claim 1, in which a compound of formula I is used in which
  R$_1$ is methyl, ethyl, CH$_3$OC(=O)CH$_2$—, CH$_3$CH$_2$OC(=O)CH$_2$—, HOCH$_2$CH$_2$—, CH$_3$CH(OH)CH$_2$— or HOCH$_2$CH(OH)CH$_2$—.

3. A process according to claim 1, in which a compound of formula I is used in which
  R$_2$ is hydrogen, methyl, ethyl or HOCH$_2$CH$_2$SCH$_2$CH$_2$C(=O)—.

4. A process according to claim 1, in which a compound of formula I is used in which the heteroaromatic residue is selected from 2-thienyl, furfuryl, 2-pyridinyl (optionally substituted), 4-pyridinyl (optionally substituted), 2-(5-methyl-1,3,4-thiadiazolyl), 2-pyrimidyl, 2-(4hydroxypyrimidyl), 2-(4-hydroxy-6-methylpyrimidyl), 2-(4hydroxy-6-propylpyrimidyl), 2-(4,6-dihydroxypyrimidyl), 2-benzoxazolyl and 2-benzothiazolyl (optionally substituted).

5. A process according to claim 1, in which a compound of formula I is used in which, independently of each other
  m is 2;
  n is at least 4, more preferably 4–50;
  p is 1;
  X is —C(=O)— or —CH$_2$C(=O)O—;
  A is methylene or ethylene;
  R$_1$ is methyl ethyl, HOCH$_2$CH$_2$—, phenyl, benzyl or 1,3,5-triazinyl;
  R$_2$ is hydrogen, methyl or HOCH$_2$CH$_2$SCH$_2$CH$_2$C(=O)—.

6. The method of claim 1, wherein brightness reduction is the yellowing of paper with time.

7. Paper produced by a process according to claim 1.

* * * * *